United States Patent
Chapaton et al.

(10) Patent No.: US 8,658,706 B2
(45) Date of Patent: Feb. 25, 2014

(54) ORGANIC SUPERACID MONOMERS CONTAINING A BIS-SULFONIC ACID GROUP AND METHODS OF MAKING AND USING THE SAME

(75) Inventors: Thomas J. Chapaton, Sterling Heights, MI (US); Tenneille Weston Capehart, Rochester Hills, MI (US); Gail Capehart, legal representative, Rochester Hills, MI (US); Armand Soldera, Sherbrooke (CA); Claude Spino, Sherbrooke (CA); Riadh Zriba, Sherbrooke (CA)

(73) Assignee: GM Global Technology Operations LLC, Detroit, MI (US)

( * ) Notice: Subject to any disclaimer, the term of this patent is extended or adjusted under 35 U.S.C. 154(b) by 155 days.

(21) Appl. No.: 13/097,484

(22) Filed: Apr. 29, 2011

(65) Prior Publication Data

US 2012/0277332 A1 Nov. 1, 2012

(51) Int. Cl.
*C08J 5/22* (2006.01)

(52) U.S. Cl.
USPC ............... 521/27; 521/25; 549/359; 556/444

(58) Field of Classification Search
USPC ..................... 521/27, 25; 549/359; 556/444
See application file for complete search history.

(56) References Cited

U.S. PATENT DOCUMENTS

| | | | |
|---|---|---|---|
| 7,393,914 B2 * | 7/2008 | Moore et al. | 528/391 |
| 7,824,918 B2 * | 11/2010 | Suri | 436/95 |
| 7,863,402 B2 * | 1/2011 | Capehart et al. | 528/171 |
| 2009/0043068 A1 * | 2/2009 | Capehart et al. | 528/171 |
| 2010/0222441 A1 * | 9/2010 | Capehart et al. | 521/25 |

OTHER PUBLICATIONS

Miyatake et al., Macromolecules, vol. 36, pp. 9691-9693 (2003).*
Zhang et al., Polymer Preprint, pp. 480-481 (1999).*

* cited by examiner

*Primary Examiner* — Peter D. Mulcahy
*Assistant Examiner* — Henry Hu
(74) *Attorney, Agent, or Firm* — BrooksGroup

(57) ABSTRACT

One embodiment includes methods of adding two sulfonic acid groups to molecules having at least two cyclic groups.

11 Claims, 1 Drawing Sheet

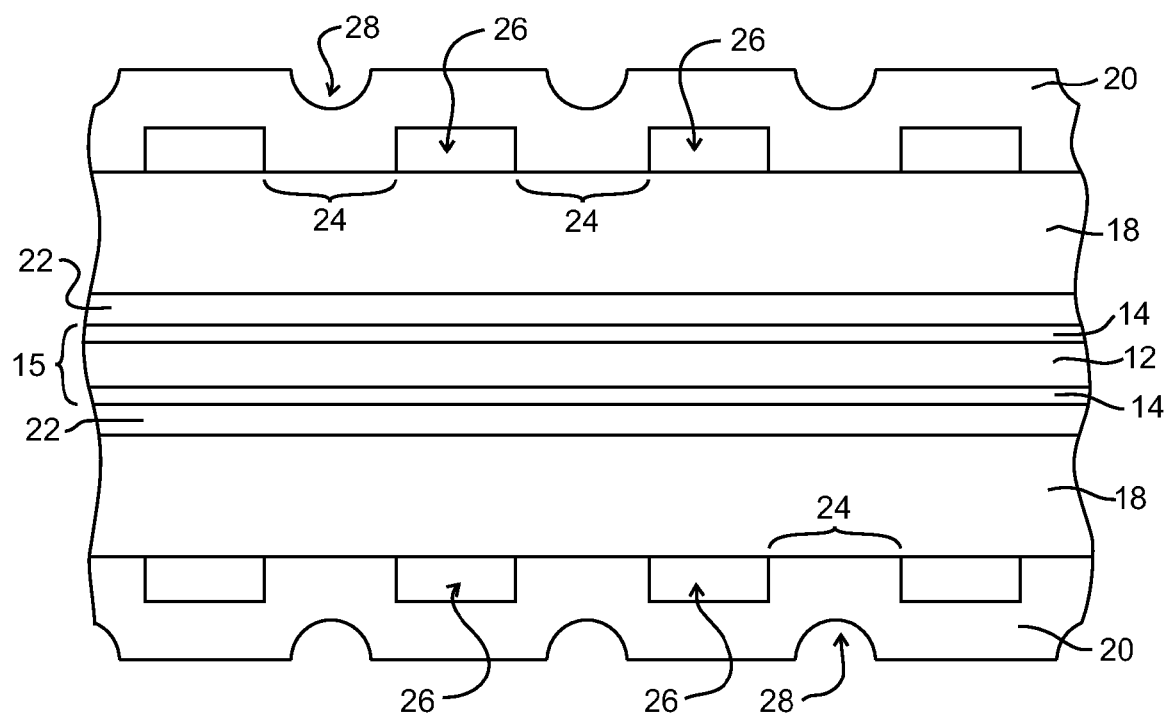

ORGANIC SUPERACID MONOMERS CONTAINING A BIS-SULFONIC ACID GROUP AND METHODS OF MAKING AND USING THE SAME

TECHNICAL FIELD

The field to which the disclosure generally relates includes cation exchange or cation conductive materials such as fuel cell electrolyte layers, products including fuel cell electrolyte layers, copolymers derived from organic superacids, and methods of making and using the same.

BACKGROUND

Monomers and prepolymers may be polymerized to make a variety of products. In some cases, it may be desirable to provide a polymer material having proton conductivity.

Many fuel cells are provided with an electrolyte layer that is sandwiched between an anode and a cathode, the assembly being known as a membrane-electrode assembly (MEA). In a proton exchange membrane (PEM) fuel cell, the electrolyte layer generally comprises a proton conducting solid phase polymer electrolyte and is often called an ion-exchange membrane or a proton exchange membrane. These polymer membranes are designed with the goal of accomplishing several functions that contribute to the overall operation of a PEM fuel cell, such as providing a conductive pathway for protons to migrate from the anode to the cathode, providing an electrical insulator between the anode and the cathode, and providing a gas impermeable layer that keeps the reactant gases separate and concentrated at their respective electrodes, to name but a few. Furthermore, the types of electrolytes associated with PEM fuel cells may be incorporated into direct methanol fuel cells (DMFC) due to similar operating conditions.

SUMMARY OF EXEMPLARY EMBODIMENTS OF THE INVENTION

In one embodiment of the invention, a monomer may comprise at least two cyclic groups and two sulfonic acid groups.

Another embodiment includes a method of making a monomer may comprise at least two cyclic groups and two sulfonic acid groups comprising transforming bis-tetrabutylammonium 2,2'-oxybis(4,5-dimethoxybenzenesulfonic acid) salt into diethyl 2,2'-oxybis(4,5-dimethoxybenzenesulfonate) with triethylamine ($Et_3N$), and adding tetrabutylammonium iodide or n-BuNI to the .diethyl 2,2'-oxybis(4,5-dimethoxybenzenesulfonate).

Another embodiment includes a method comprising introducing two thiol units into 2,2'-oxybis(4,5-dimethobenzenesulfonyl)ether followed by oxidation to produce 2,2'-oxybis(4,5-dimethoxybenzene thiol)

Another embodiment includes a method comprising oxidizing 2,2'-oxybis(4,5-dimethoxybenzene thiol) to produce 2,2'-oxybis(4,5-dimethoxybenzenesulfonic acid).

Another embodiment includes a method comprising chlorosulfonating 1,1'-oxybis[4-(R-oxy)-3-methoxybenzene] to produce 2,2'-oxybis[5-(R-oxy)-4-methoxybenzenesulfonyl chloride], converting the 2,2'-oxybis[5-(R-oxy)-4-methoxybenzenesulfonyl chloride] to diethyl 2,2'-oxybis[5-(R-oxy)-4-methoxybenzenesulfonate], deprotecting the alcohols in the presence of tetrabutylammonium iodide or n-BuNI to produce bis-tetrabutylammonium 2,2'-oxybis(5-hydroxy-4-methoxybenzenesulfonic acid) salt.

Another embodiment includes a method comprising chlorosulfonating 1,1'-oxybis[3-(R-oxy)-4-methoxybenzene] to produce 2,2'-oxybis[4-(R-oxy)-5-methoxybenzenesulfonyl chloride], converting the 2,2'-oxybis[4-(R-oxy)-5-methoxybenzenesulfonyl chloride] to diethyl 2,2'-oxybis[4-(R-oxy)-5-methoxybenzenesulfonyl chloride], deprotecting the alcohols in the presence of tetrabutylammonium iodide or n-BuNI to produce bis-tetrabutylammonium 2,2'-oxybis(4-hydroxy-5-methoxybenzenesulfonic acid) salt.

Another embodiment includes the compound diethyl 2,8-dimethoxy-3,7-dioxodibenzo[b,d]furan-9a,9b(3H,7H)-disulfonate.

Another embodiment includes a method comprising oxidizing diethyl 2,2'-oxybis(4-hydroxy-5-methoxybenzenesulfonate) to produce 2,8-dimethoxy-3,7-dioxodibenzo[b,d]furan-9a,9b(3H,7H)-disulfonate.

Polymerizing the Monomers

Membranes Having Repeating Units of the Monomers

Other exemplary embodiments of the invention will become apparent from the detailed description provided hereinafter. It should be understood that the detailed description and specific examples, while disclosing exemplary embodiments of the invention, are intended for purposes of illustration only and are not intended to limit the scope of the invention.

BRIEF DESCRIPTION OF THE DRAWINGS

FIG. 1 illustrates a product according to one embodiment of the invention.

DETAILED DESCRIPTION OF EXEMPLARY EMBODIMENTS

The following description of the embodiment(s) is merely exemplary in nature and is in no way intended to limit the invention, its application, or uses.

It is contemplated that an organic based proton exchange membrane comprising a solid phase organic based polymer material may be incorporated into various types of fuel cells to serve as an electrolyte layer situated between an anode layer and a cathode layer. In one embodiment, fuel cell performance may be enhanced by providing an organic based proton exchange membrane that exhibits improved proton conductivity at a low relative humidity. Allowing fuel cells to operate at a low relative humidity may reduce the problems associated with cathode flooding, water management and freeze start up, and possibly lower the cost of operating a fuel cell.

A variety of properties associated with the organic based polymer material that constitutes the organic based proton exchange membrane may contribute to an elevated and maintainable volumetric density of solvated protons which ultimately provides for improved proton conductivity. These properties may include one or more of, for instance, the presence of one or more high acidity acid groups represented by a relatively high acid dissociation constant ($K_a$), the presence of one or more acid groups capable of deprotonating at a relatively low molar ratio of water to acid sites (A), or a low molar volume of the acid moiety.

In one embodiment, a PEM fuel cell may comprise an organic based proton exchange membrane comprising a solid phase organic based copolymer material comprising at least one structural unit derived from a organic superacid capable of undergoing a polycondensation reaction with a second monomer. The term "superacid" as used herein means an acid having an acidity greater than 100% sulfuric acid. In one embodiment, the superacid may have two or more acid groups, such as a super diacid. In another embodiment, a plurality of organic super diacid structural units may be polymerized with a plurality of suitable and indistinguishable monomer units, or a mixture of suitable and chemically distinguishable monomer units, to form an alternating, random, or block copolymer strand. In another embodiment, a plurality of organic super diacid structural units may be present in hydrophilic polymer block segments that are subsequently linked with one or more suitable hydrophobic monomers or polymer block segments to form a linear or branched n-block copolymer strand where n≥2. In one embodiment, a triblock copolymer strand may include any linear arrangement of a hydrophilic organic super diacid polymer block segment linked between a first hydrophobic polymer block segment and a second hydrophobic polymer block segment. In yet another embodiment, several hydrophilic organic super diacid polymer block segments may be linked with multiple hydrophobic polymer block segments to form a random multiblock copolymer strand. Additionally, it is possible to form an organic based proton exchange membrane comprising a polymer material that has a monodispersed polymer composition comprising the alternating, random, n-block, or multiblock copolymer strands mentioned above. A method for producing a polymer material suitable for use as a proton exchange membrane that comprises copolymer strands synthesized in part from a plurality of organic super diacid structural units will be discussed in more detail at a later point. The particular organic super diacids suitable for use in such a method will now be described.

In one embodiment, an organic super diacid structural unit may be derived from an organic super diacid characterized by a strong acidity and capable of participating in a polycondensation reaction. The strong acidity may be attributed wholly or in-part to a molecular structure that promotes strong intramolecular hydrogen bonding between two acid groups in close spatial proximity. This hydrogen bonding may be supplemented by the positioning of OH, or other useful groups, in the diacid structure. Acidity may be further enhanced by molecular structures having electron withdrawing groups (EWG) linking the phenyl groups of the diacids. The strong acidity exhibited by the organic super diacid contributes to the ability of the super diacid to deprotonate at relatively low molar ratios of water to acid sites (A).

One embodiment includes methods of making monomers having at least two cyclic organic groups and functional acid groups. The monomers may include free alcohol function making them suitable for polymerizing into proton exchange membranes. Another embodiment includes a method of incorporating two sulfonic functional groups in aromatic groups (Scheme 1) of molecules 1-5 (2,3,7,8-tetramethoxydibenzo[b,d]furan ($C_{16}H_{16}O_5$, wherein X=_ (i.e., no constituent); 2,3,7,8-tetramethoxyoxanthrene ($C_{16}H_{16}O_6$, wherein X=O); 2,3,7,8-tetramethoxyphenoxathiine ($C_{16}H_{16}O_5S$, wherein X=S); 2,3,7,8-tetramethoxyphenoxathiine 10,10-dioxide ($C_{16}H_{16}O_7S$, wherein X=$SO_2$); 2,3,7,8-tetramethoxy-10,10-dimethyl-10H-phenoxasiline ($C_{18}H_{22}O_5Si$, wherein X=$Si(CH_3)_2$, respectively) to produce molecules 6-10 (2,3,7,8-tetramethoxydibenzo[b,d]furan-4,6-disulfonic acid ($C_{16}H_{16}O_{11}S_2$, wherein X=_ (i.e., no constituent)); 2,3,7,8-tetramethoxyoxanthrene-1,9-disulfonic acid ($C_{16}H_{16}O_{12}S_2$ wherein X=O); 2,3,7-tetramethoxyphenoxathiine-4,6-disulfonic acid ($C_{16}H_{16}O_{11}S_3$ wherein X=S0; 2,3,7,8-tetramethoxyphenoxathiine-4,6-disulfonic acid 10,10-dioxide ($C_{16}H_{16}O_{13}S_3$ wherein X=$SO_2$); 2,3,7,8-tetramethoxy-10,10-dimethyl-10H-phenoxasiline-4,6-disulfonic acid ($C_{18}H_{22}O_{11}S_2Si$, wherein X=$Si(CH_3)_2$), respectively), as shown below.

Scheme 1: Proposed designed novel monomers.

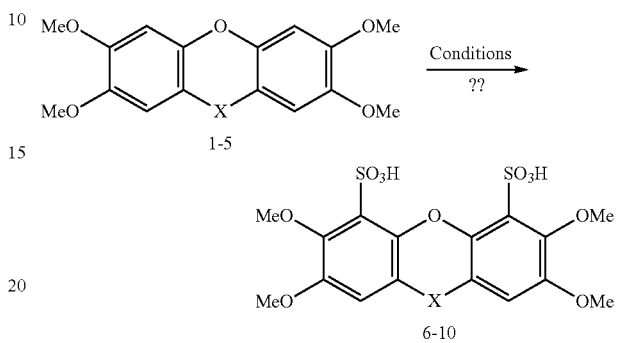

(wherein X in the reaction scheme above is one of no constituent, O, S, $SO_2$, $Si(CH_3)_2$)

Where X = _, O, S, $SO_2$, $Si(CH_3)_2$

Another embodiment includes a method including reacting bis(3,4-dimethoxyphenyl)ether (compound 11: $C_{16}H_{18}O_5$) with chlorosulfonic acid ($ClSO_3H$) to produce 2,2'-oxybis(4,5-dimethoxybenzenesulfonyl chloride) (compound 12: $C_{16}H_{16}Cl_2O_9S_2$) (Scheme 2). This bis-sulfonyl chloride product (compound 12: $C_{16}H_{16}Cl_2O_9S_2$) was perceived as an ideal synthesis prospect candidate to achieve the formation of compounds (compound 6: ($C_{16}H_{16}O_{11}S_2$ X=))_(7: ($C_{16}H_{16}O_{12}S_2$ X=O)), (compound 8: $C_{16}H_{16}O_{11}S_3$ X=S), (compound 9: $C_{16}H_{16}O_{13}S_3$ X=$SO_2$), and (compound 10: $C_{18}H_{22}O_{11}S_2Si$ X=$Si(CH_3)_2$.) It is important to note that the insertion of the bis-sulfonic acid moiety occurs relatively late during the synthesis of the core, thus lessening the number of reactions in the presence of highly acidic functional groups.

Scheme 2: Chlorosulfonation of the aromatic.

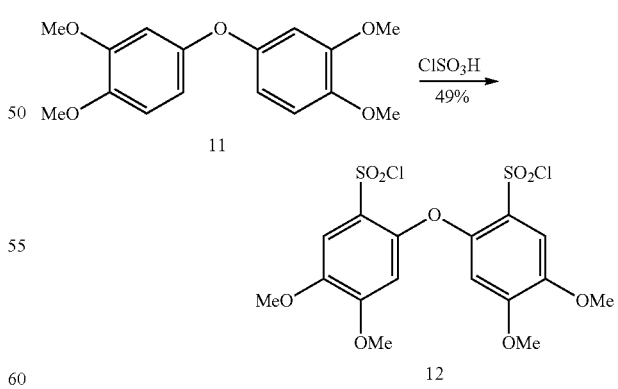

Select embodiments include two synthetic routes to introduce a bis-sulfonic acid function. Synthetic route use of chlorosulfonic acid ($ClSO_3H$), which yields a sulfonic acid (R—S(=O)$_2$—OH) group[3] or a sulfonyl chloride (R—$SO_2$—Cl) group[4] in only one step, is shown below.

Scheme 3: Proposed synthetic route 1.

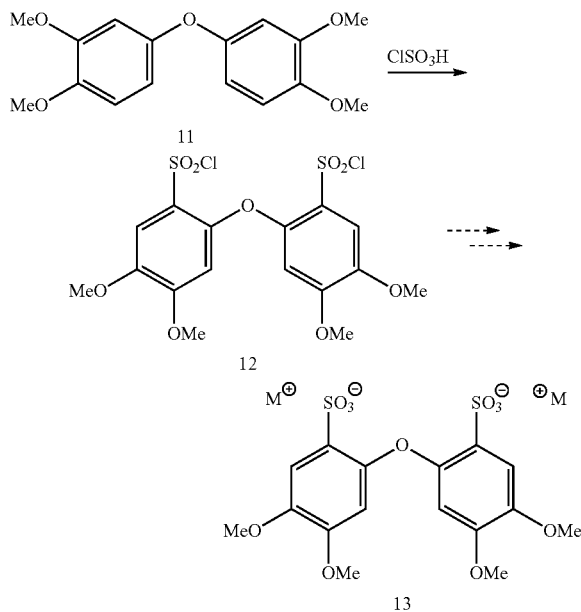

Synthetic route 2, which uses a Charles Mioskowski's Reagent (CMR)[5] introduces two thiol units, as shown in 2,2'-oxybis(4,5-dimethoxybenzene thiol) (compound 14: $C_{16}H_{18}O_5S_2$). The 2,2'-oxybis(4,5-dimethoxybenzene thiol) (compound 14: $C_{16}H_{18}O_5S_2$) can subsequently be oxidized to the desired 2,2'-oxybis(4,5-dimethoxybenzenesulfonic acid) (compound 15: $C_{16}H_{18}O_{11}S_2$) (Scheme 4).

Scheme 4: Proposed synthetic route 2.

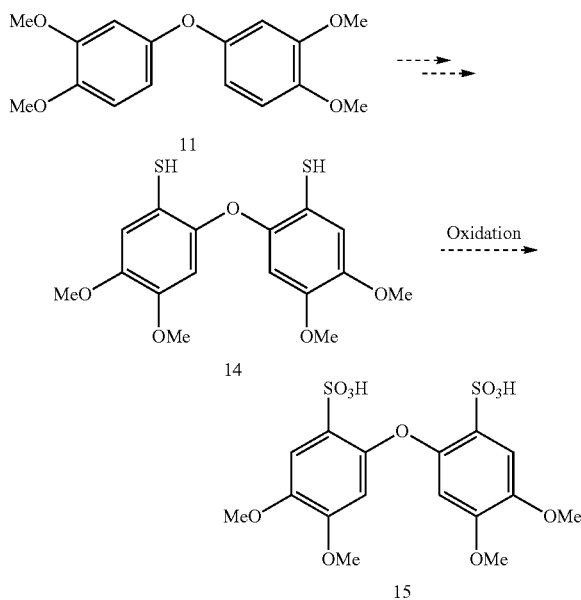

Another embodiment includes a method including transforming 2,2'-oxybis(4,5-dimethoxybenzenesulfonyl chloride) (compound 12: $C_{16}H_{16}Cl_2O_9S_2$) into diethyl 2,2'-oxybis(4,5-dimethoxybenzenesulfonate) (compound 23: $C_{20}H_{26}O_{11}S_2$) with triethylamine ($Et_3N$) in ethanol (EtOH). Second, by adding 2 equivalents of tetrabutylammonium iodide (TBAI or n-BuNI)[8] to 1 equivalent of diethyl 2,2'-oxybis(4,5-dimethoxybenzenesulfonate) (compound 23: $C_{20}H_{26}O_{11}S_2$) during reflux conditions in acetone to produce bis-tetrabutylammonium 2,2'-oxybis(4,5-dimethoxybenzenesulfonic acid) salt (compound 24: $(C_{16}H_{16}O_{11}S_2)^{2-}.2[(C_4H_9)_4N]^+$) (Scheme 10). Another embodiment includes a method including polymerizing the bis-tetrabutylammonium 2,2'-oxybis(4,5-dimethoxybenzenesulfonic acid) salt (compound 24: $(C_{16}H_{16}O_{11}S_2)^{2-}.2[(C_4H_9)_4N]^+$) and the resulting polymer can then be acidified to produce a acidic membrane as desired.

Scheme 10: Procedure to attain bis-tetrabutylammonium bis-sulfonic acid salt (compound 24: $(C_{16}H_{16}O_{11}S_2)^{2-}\cdot 2[(C_4H_9)_4N]^+$).

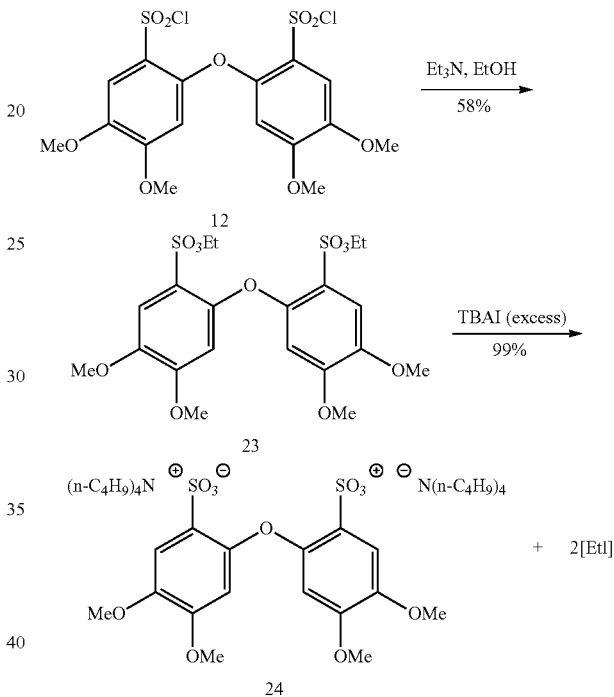

Another embodiment include the treatment of 1,1'-oxybis (3,4-dimethoxybenzene (compound 11: $C_{16}H_{18}O_5$) with CMR. When CMR is in the presence of triflic anhydride ($TfO_2$) and 1,1'-oxybis(3,4-dimethoxybenzene (compound 11: $C_{16}H_{18}O_5$), followed by the addition of excess triethylamine ($Et_3N$), this produces the intermediate dimethyl 3,3'-{oxybis[(4,5-dimethoxybenzene-2,1-diyl)sulfanediyl]} dipropanoate (compound 25: $C_{24}H_{30}O_9S_2$). Which, after an elimination step by potassium tert-butoxide (t-BuOK), gave the desired 2,2'-oxybis(4,5-dimethoxybenzene thiol) (compound 14: $C_{16}H_{18}O_5S_2$). Molecule (compound 14: $C_{16}H_{18}O_5S_2$) may be subsequently oxidized to yield a corresponding sulfonic acid after polymerization.

Scheme 11: Procedure to attain the ether thiol (compound 14: $C_{16}H_{18}O_5S_2$).

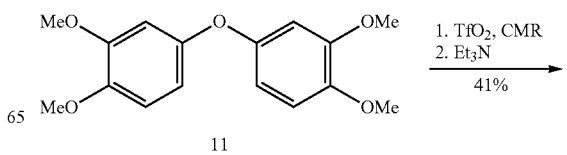

-continued

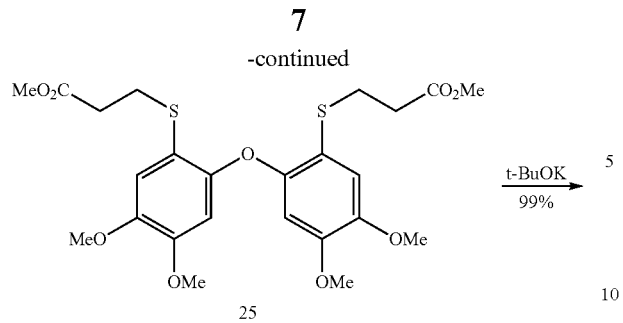

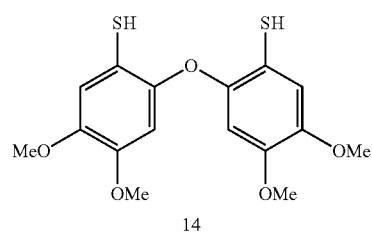

The best way to make the bis sulfonic acid salt (compound 13: $(C_{16}H_{16}O_{11}S_2)^{2-} \cdot 2[M]^+$) polymerizable is to substitute two of the four methoxy groups with two hydroxyl groups. There are thus two possible choices: first, the alcohol functions are in position 5 and 5' as in bis-(M) 2,2'-oxybis(5-hydroxy-4-methoxybenzenesulfonic acid) salt (compound 27: $(C_{14}H_{12}O_{11}S_2)^{2-} \cdot 2[M]^+$), which could be made from 1,1'-oxybis[4-(R-oxy)-3-methoxybenzene] (compound 28: R—$(C_{14}H_{12}O_5)$—R); second, the alcohol functions are in position 4 and 4' as in bis-(M) 2,2'-oxybis(4-hydroxy-5-methoxybenzenesulfonic acid) salt (compound 29: $(C_{14}H_{12}O_{11}S_2)^{2-} \cdot 2[M]^+$), which could be made from 1,1-oxybis[3-(R-oxy)-4-methoxybenzene] (compound 30: R—$(C_{14}H_{12}O_5)$—R) (Scheme 12).

-continued

The starting ethers (compound 28: R—$(C_{14}H_{12}O_5)$—R) or (compound 30: R—$(C_{14}H_{12}O_5)$—R) may be obtained using the UCR (Ullmann Coupling Reaction) between a phenol and an aromatic bromide. Each of these molecules possesses two protected alcohol functions. Then, chlorosulfonation of the ethers (compound 28: R—$(C_{14}H_{12}O_5)$—R) or (compound 30: R—$(C_{14}H_{12}O_5)$—R) would lead to the corresponding 2,2'-oxybis[5-(R-oxy)-4-methoxybenzenesulfonyl chloride] (compound 31: R—$(C_{14}H_{10}Cl_2O_9S_2)$—R) or 2,2'-oxybis[4-(R-oxy)-5-methoxybenzenesulfonyl chloride] (compound 32: R—$(C_{14}H_{10}Cl_2O_9S_2)$—R), respectively (Scheme 13). These sulfonyl chlorides could be converted to diethyl 2,2'-oxybis[5-(R-oxy)-4-methoxybenzenesulfonate] (compound 33: R—$(C_{19}H_{22}O_{10}S_2)$—R) or diethyl 2,2'-oxybis[4-(R-oxy)-5-methoxybenzenesulfonate] (compound 34: R—$(C_{19}H_{22}O_{10}S_2)$—R), respectively (Scheme 13). Finally, after deprotection of the alcohols, one equivalent of the bis-tetrabutylammonium 2,2'-oxybis(5-hydroxy-4-methoxybenzenesulfonic acid) salt (compound 35: $(C_{14}H_{12}O_{11}S_2)^{2-} \cdot 2[(C_4H_9)_4N]^+$) or bis-tetrabutylammonium 2,2'-oxybis(4-hydroxy-5-methoxybenzenesulfonic acid) salt (compound 36: $(C_{14}H_{12}O_{11}S_2)^{2-} \cdot 2[(C_4H_9)_4N]^+$) may be obtained by the reaction with two equivalents of TBAI, accordingly (Scheme 13). The resulting products may then be co-polymerized with a suitable linker and acidified to give the desired membrane.

Scheme 12: Retrosynthesis of polymerizable monomers (compound 28: R—$(C_{14}H_{12}O_5)$—R) and (compound 30: R—$(C_{14}H_{12}O_5)$—R).

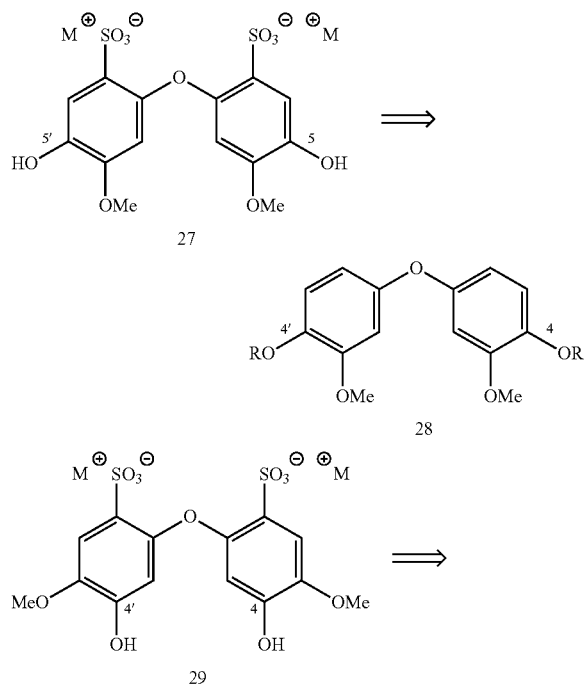

Scheme 13:

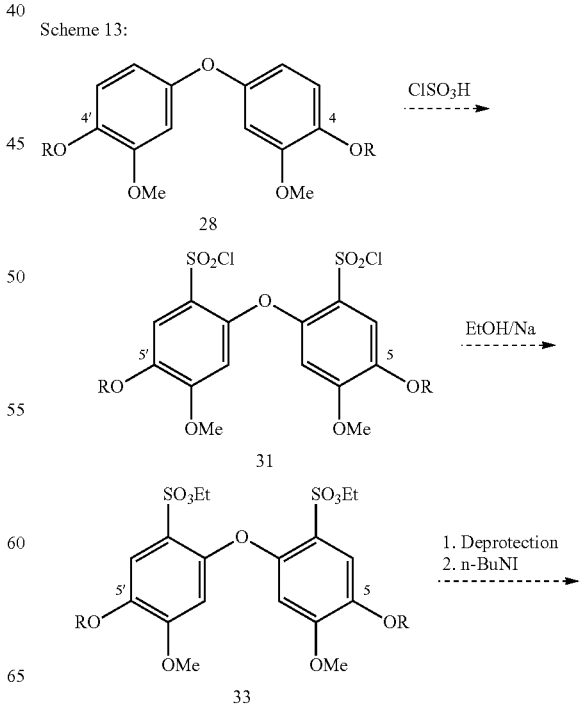

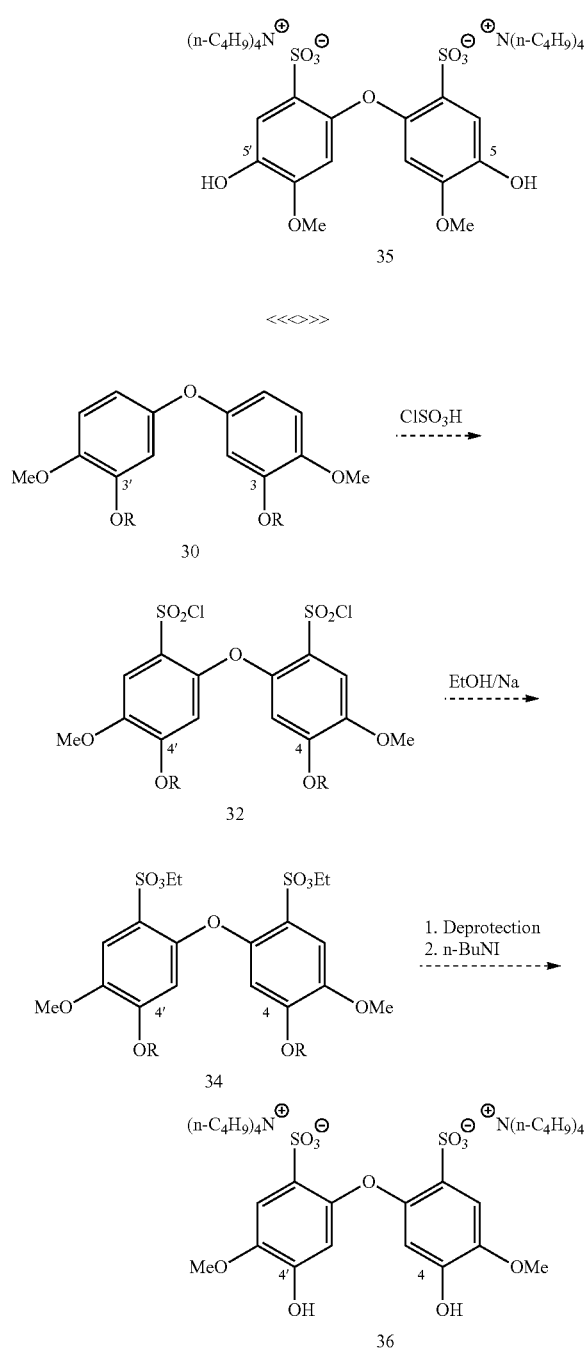

Proposed syntheses for bis-tetrabutylammonium oxybis-sulfonic acid salts (compound 35: $(C_{14}H_{12}O_{11}S_2)^{2-}\cdot 2[(C_4H_9)_4N]^+)$ and (compound 36: $(C_{14}H_{12}O_{11}S_2)^{2-}\cdot 2[(C_4H_9)_4N]^+)$.

Another embodiment includes the synthesis of oxybis-sulfonate salts. The UCR of 4-bromo-1-methoxy-2-(propan-2-yloxy)benzene (compound 64: $C_{10}H_{13}BrO_2$) [(obtained in four steps from guaiacol (compound 43: $C_7H_8O_2$)] and 4-methoxy-3-(propan-2-yloxy)phenol (compound 65: $C_{10}H_{14}O_3$) [obtained in three steps from isovanillin (compound 40: $C_8H_8O_3$)] under the usual conditions led to 1,1'-oxybis[4-methoxy-3-(propan-2-yloxy)benzene] (compound 66: $C_{20}H_{26}O_5$) with an average yield of 50% (Scheme 20).

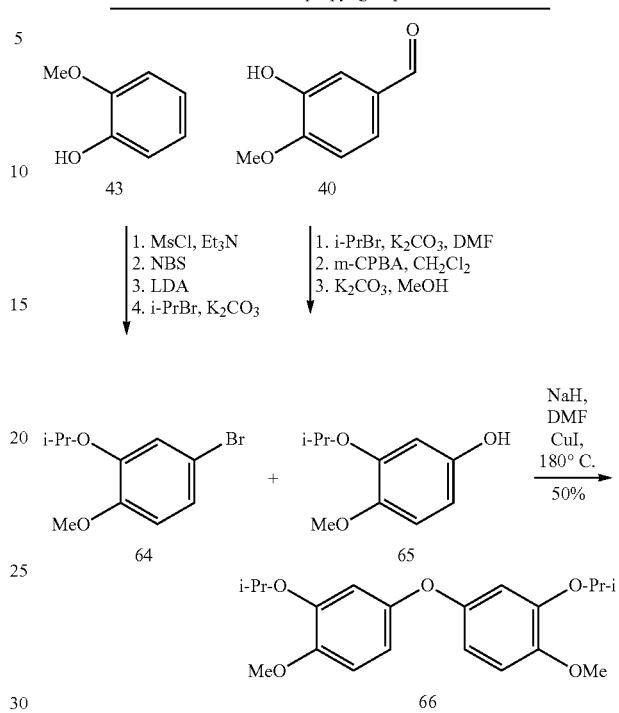

The 1,1'-oxybis[4-methoxy-3-(propan-2-yloxy)benzene] (compound 66: $C_{20}H_{26}O_5$) was converted to the corresponding 2,2'-oxybis(4-hydroxy-5-methoxybenzenesulfonyl chloride) (compound 67: $C_{14}H_{12}Cl_2O_9S_2$) by the addition of chlorosulfonic acid, with an average yield of 71% (Scheme 21). The deprotection of the alcohol functions also occurred concomitantly. After several tests and an optimization procedure, diethyl 2,2'-oxybis(4-hydroxy-5-methoxybenzene sulfonate) (compound 68: $C_{18}H_{22}O_{11}S_2$) was isolated in an average yield of 70% using the pair EtOH/NaH in THF.

Scheme 21: Chlorosulfonation of 66.

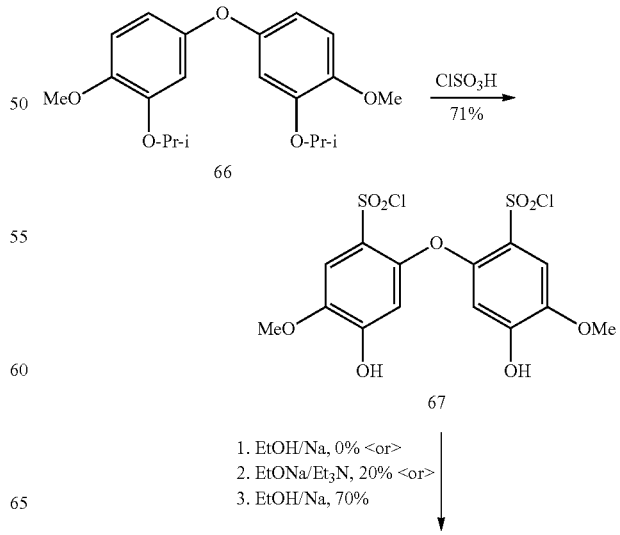

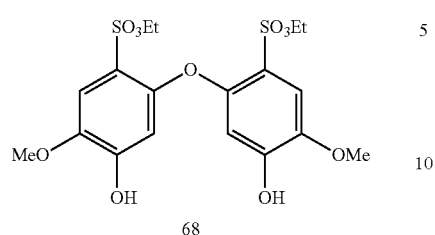
68

Using this new procedure, we went back and converted bis-sulfonyl chloride (compound 60: $C_{14}H_{12}O_2O_9S_2$) to ethylsulfonate (compound 61: $C_{18}H_{22}O_{11}S_2$) resulting in a 52% yield (Scheme 22).

The ethylsulfonates (compound 61: $C_{18}H_{22}O_{11}S_2$) and (compound 68: $C_{18}H_{22}O_{11}S_2$) were converted to their resulting bis-tetrabutylammonium oxybis-sulfonic acid salts (compound 35: $(C_{14}H_{12}O_{11}S_2)^{2-}.2[(C_4H_9)_4N]^+)$ and (compound 36: $(C_{14}H_{12}O_{11}S_2)^{2-}.2[(C_4H_9)_4N]^+)$ using TBAI (Scheme 23).

Scheme 23. Final reaction steps for monomers (compound 35: $(C_{14}H_{12}O_{11}S_2)^{2-}\cdot 2[(C_4H_9)_4N]^+)$ and (compound 36: $(C_{14}H_{12}O_{11}S_2)^{2-}\cdot 2[(C_4H_9)_4N]^+)$.

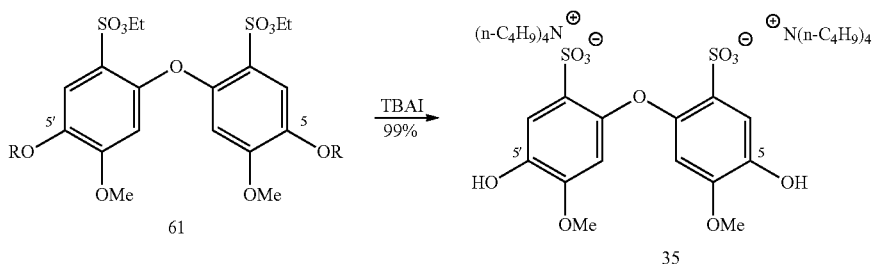

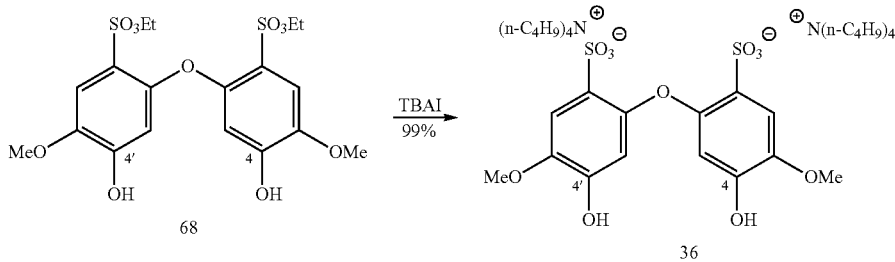

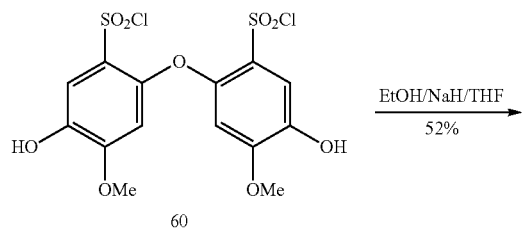

Scheme 22. Conversion of (compound 60: $C_{14}H_{12}Cl_2O_9S_2$) to (compound 61: $C_{18}H_{22}O_{11}S_2$) using the new procedure Finally, the two long sought oxybis-sulfonic acid salt types (compound 27: $(C_{14}H_{12}O_{11}S_2)^{2-}.2[M]^+)$, and (compound 29: $(C_{14}H_{12}O_{11}S_2)^{2-}.2[M]^+)$ were originally obtained from vanillin (compound 37: $C_8H_8O_3$) and isovanillin (compound 40: $C_8H_8O_3$), respectively. This was accomplished with sufficient quantitative yields using the reactions described in the previous Schemes.

Another embodiment includes a method of making a new tricyclic monomer called bis(M) 1,9-dihydroxy-2,8-dimethoxydibenzo[b,d]furan-4,6-disulfonic acid salt (compound 69: $(C_{14}H_{10}O_{11}S_2)^{2-}.2[M]^+)$ from precursor (compound 68: $C_{18}H_{22}O_{11}S_2$) (Scheme 24).

Scheme 24: Retrosynthetic scheme to (compound 69: $(C_{14}H_{10}O_{11}S_2)^{2-} \cdot 2[M]^+$).

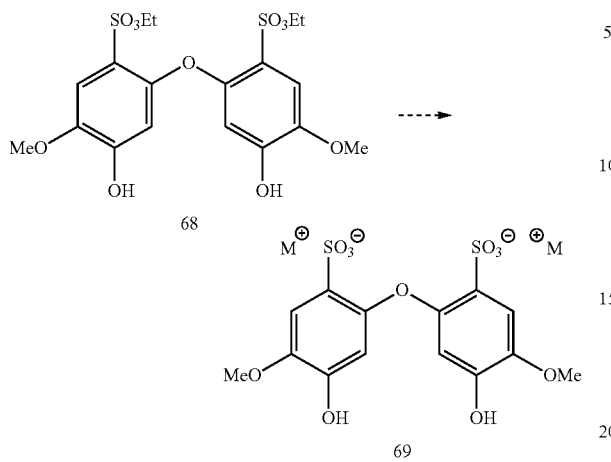

Oxidation of molecule (compound 68: $C_{18}H_{22}O_{11}S_2$) may lead to two different aryloxy radicals; diethyl 2,2'-oxybis(4-oxy-radical-5-methoxybenzenesulfonate) (compound 70: $(C_{18}H_{20}O_{11}S_2)^{2-}$.) and diethyl 2,2'-oxybis(3-aryl-radical-5-methoxy-4-oxocyclohexa-1,5-diene-1-sulfonate) (compound 71: $(C_{18}H_{20}O_{11}S_2)^{2-}$.), which is drawn in two resonance forms. The radical may collapse to diethyl 1,9-dihydroxy-2,8-dimethoxydibenzo[b,d]furan-4,6-disulfonate (compound 72: $C_{18}H_{20}O_{11}S_2$), after coupling and re-aromatization.

Scheme 25: Intramolecular oxidative coupling of (compound 72: $C_{18}H_{20}O_{11}S_2$).

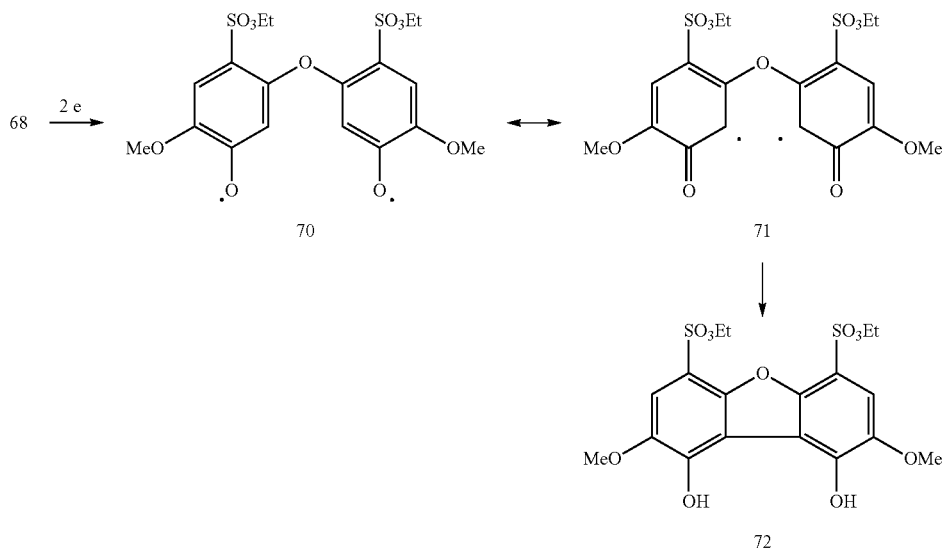

Various reducing agents were tested (e.g., FeCl$_3$[11], ZnCl$_2$ [K$_3$Fe(CN)$_6$][12], PIFA[13], etc.) in different solvents to generate the two aryloxy radicals. The results are presented in Table 2. Unfortunately, the precursor (compound 72: $C_{18}H_{20}O_{11}S_2$) was never obtained. Strangely, under some conditions, the tricyclic compound called diethyl 2,8-dimethoxy-3,7-dioxodibenzo[b,d]furan-9a,9b(3H,7H)-disulfonate (compound 73: $C_{18}H_{20}O_{11}S_2$) was formed in high yield (Scheme 26).

Scheme 26: Oxidative coupling of compound (compound 68: $C_{18}H_{22}O_{11}S_2$).

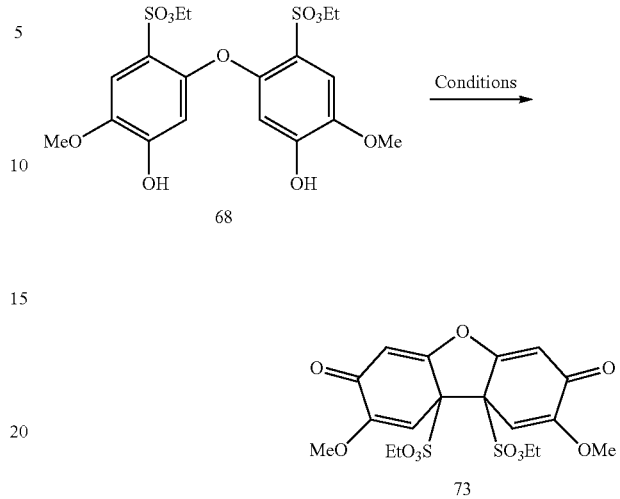

Another embodiment includes the synthesis of polymerizable tricyclic monomers, similar to the skeleton backbone compounds (compound 1: $C_{16}H_{16}O_5$ X=_) and (compound 6: $C_{16}H_{16}O_{11}S_2$ X=_) (where Y=O) shown in Scheme 33.

Scheme 33. Structure of the tricyclic monomers.

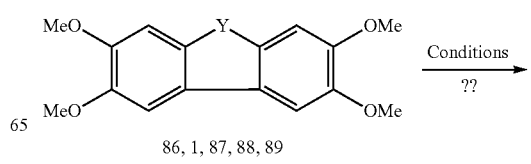

86, 1, 87, 88, 89

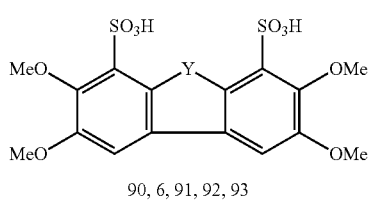

Where Y = _, O, S, SO$_2$, Si(CH$_3$)$_2$

The skeleton compounds drawn in Scheme 33 use similar logic to those found in Scheme 1. Compounds (compound 86: C$_{16}$H$_{16}$O$_4$ Y=_) and (compound 90: C$_{16}$H$_{16}$O$_{10}$S$_2$ Y=_) were not pursued, due to the inherent spatial orientation of their sulfonic acid groups. Compounds (compound 87: C$_{16}$H$_{16}$O$_4$S Y=S), (compound 88: C$_{16}$H$_{16}$O$_6$S Y=SO$_2$), (compound 89: C$_{18}$H$_{22}$O$_4$Si Y=Si(CH$_3$)$_2$), (compound 91: C$_{16}$H$_{16}$O$_{10}$S$_3$ Y=S), (compound 92: C$_{16}$H$_{16}$O$_{12}$S$_3$ Y=SO$_2$—), and (compound 93: C$_{18}$H$_{22}$O$_{10}$S$_2$Si Y=Si(CH$_3$)$_2$) will most likely be investigated at a future time.

Initial attempts to synthesize 2,3,7,8-tetramethoxydibenzo[b,d]furan (compound 1: C$_{16}$H$_{16}$O$_5$ X=_) were carried out using intramolecular coupling on 1,1'-oxybis(2-bromo-4,5-dimethoxybenzene) (compound 20: C$_{16}$H$_{16}$Br$_2$O$_5$) placed under UCR conditions in the presence of deactivated copper (0) (Scheme 34). This first attempt resulted in a 5% yield of monomer (compound 1: C$_{16}$H$_{16}$O$_5$ X=_) product. However, this result could not be reproduced, even using activated copper (copper powder can be more reactive thorough an acidic treatment to eliminate any oxidized copper).

Scheme 34. First attempt synthesis of monomer (compound 1: C$_{16}$H$_{16}$O$_5$ X=_).

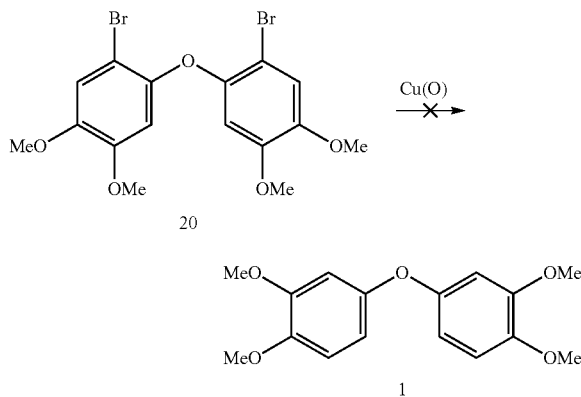

A second synthetic route to create monomer (compound 1: C$_{18}$H$_{18}$O$_5$ X=_) was carried out successfully, by reacting 2-methoxyhydroquinone (compound 94: C$_7$H$_8$O$_3$) with 1,4-benzoquinone (compound 95: C$_6$H$_4$O$_2$) in acetic acid[15] during refluxing conditions (Scheme 35). A 40% yield of the desired tricyclic molecule 3,7-dimethoxydibenzo[b,d]furan-2,8-diol (compound 96: C$_{14}$H$_{12}$O$_5$) was obtained. The alcohol functions of (compound 96: C$_{14}$H$_{12}$O$_5$) were protected with different groups in order to test the subsequent sulfonation reaction (see the experimental section for details of each of these protections).

Scheme 35. Preparation of compounds (compound 1: C$_{16}$H$_{16}$O$_5$ X=_), (compound 97: C$_{20}$H$_{20}$O$_5$), (compound 98: C$_{18}$H$_{16}$O$_7$) and (compound 99: C$_{28}$H$_{24}$O$_5$).

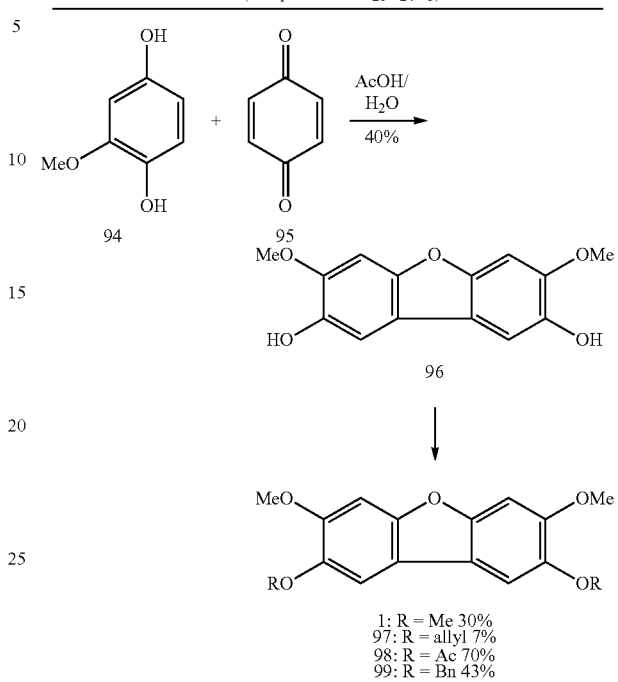

1: R = Me 30%
97: R = allyl 7%
98: R = Ac 70%
99: R = Bn 43%

Those skilled in the art are capable of manipulating the organic super diacid polymer synthesis process to form copolymers that comprise an alternating copolymer, an n-block copolymer where 2≤n≥5, or a random multiblock copolymer. For example, commonly assigned United States Patent Applications 2004/0186262 filed Jan. 30, 2004 and 2006/0249444 filed May 3, 2005 both disclose block copolymer teachings that may be useful in conjunction with the organic superacids disclosed herein for fabricating organic based B2 proton exchange membranes.

Referring now to FIG. 1, one embodiment of the invention may include a fuel cell 10 including an electrolyte layer 12 comprising an organic based proton exchange membrane fabricated from the organic polymer structures previously discussed. The organic based proton exchange membrane may be in various types of fuel cells, such as proton exchange membrane fuel cells and direct methanol fuel cells.

The fuel cell 10 is an electrochemical device that combines a fuel such as hydrogen with an oxidant such as oxygen to produce electricity. The fuel cell 10 may include an electrolyte layer 12 sandwiched between two electrode layers 14, the combination being known as a membrane electrode assembly (MEA) 15. In practice, the electrode layers 14 are further defined as an anode and a cathode, both of which facilitate chemical reactions that occur in the fuel cell 10. The anode is defined as the electrode layer 14 that electrons flow away from and the cathode is defined as the electrode layer 14 that electrons flow towards.

The electrode layers 14 generally may include small catalyst particles mixed with a binder such as an ionomer. The binder serves to fix the catalyst particles in a structure that allows for optimal contact between the catalyst particles contained in the electrodes 14 and the electrolyte 12. In one embodiment, the binder may include the types of organic super acid based copolymers disclosed herein. Platinum metals and platinum alloys are popular examples of catalyst particles and may be utilized as either a pure catalyst or a supported catalyst. In the case of a supported catalyst, the small catalyst particles may be finely divided over larger carbon or graphite support particles.

Gas diffusion layers (GDL) 18 are situated alongside the surfaces of the electrode layers 14 that are furthest from the electrolyte layer 12. GDL's 18 serve numerous functions and may include carbon-based materials that render the layer porous and conductive. A GDL 18 comprises a porous media to assist in diffusing the reactant gases equally across their respective electrode layers 14, as well as to move water or any other liquid away from the electrode layers 14. The porous media of the GDL 18 is also conductive to provide an electrical pathway from the electrode layers 14 to the current collector so that the electrons generated at the anode can be extracted from the fuel cell 10 and eventually returned to the cathode. A further function of the GDL 18 is to provide a basic mechanical structure for the MEA 15. Typically, carbon-based materials that make up a GDL 18 may include, but are not limited to, carbon cloth, non-woven pressed carbon fibers, carbon paper, or a felt-like carbon material.

It is also common to add various materials to a GDL 18. For example, GDL's 18 may include a microporous layer 22 interposed between the GDL 18 and the electrode layer 14 to assist in water management within a fuel cell 10. A microporous layer 22 may include a binder and some other component that influences the binder's affinity towards water.

To produce a useful voltage, many fuel cells 10 may be connected in series to form a fuel cell stack. A common approach to form a fuel cell stack is to connect adjacent fuel cells 10 through a bipolar plate 20. A bipolar plate 20 may form an electrical connection 24 over a large portion of the GDL layer 18 so as to minimize the electrical resistance that leads to a voltage drop when an electron travels between the bipolar plate 20 and the electrode layer 14. At the same time, a bipolar plate 20 provides reactant gas flow channels 26 for separately feeding a fuel to the anode and an oxidant to the cathode. To satisfy these two competing interests, the gas flow channels 26 are sized to allow a sufficient amount of fuel or oxidant to be supplied to the electrode layer 14 while at the same time providing adequate surface contact with the GDL layer 18 to facilitate the transfer of electrons. A bipolar plate 20 may also include coolant flow channels 28 that can support the flow of a coolant vapor or a coolant liquid if necessary. Bipolar plates 20 may include a conductive material such as, but not limited to, graphite, a polymeric carbon composite, stainless steel, aluminum, titanium, or combinations thereof.

The above description of embodiments of the invention is merely exemplary in nature and, thus, variations thereof are not to be regarded as a departure from the spirit and scope of the invention.

What is claimed is:

1. A method comprising chlorosulfonating at least one of (2,3,7,8-tetramethoxydibenzo[b,d]furan; 2,3,7,8-tetramethoxyoxanthrene; 2,3,7,8-tetramethoxyphenoxathiine; 2,3,7,8-tetramethoxyphenoxathiine 10,10-dioxide; 2,3,7,8-tetramethoxy-10,10-dimethyl-10H-phenoxasiline or 1,1'-oxybis(3,4-dimethoxybenzene) to produce a resulting product having at least 2 sulfonic groups per molecule.

2. The method as set forth in claim 1 comprising chlorosulfonating (2,3,7,8-tetramethoxydibenzo[b,d]furan to produce (2,3,7,8-tetramethoxydibenzo[b,d]furan-4,6-disulfonic acid.

3. The method as set forth in claim 1 comprising chlorosulfonating 2,3,7,8-tetramethoxyoxanthrene to produce 2,3,7,8-tetramethoxyoxanthrene-1,9-disulfonic acid.

4. The method as set forth in claim 1 comprising chlorosulfonating 2,3,7,8-tetramethoxyphenoxathiine to produce 2,3,7,8-tetramethoxyphenoxathiine-4,6-disulfonic acid.

5. The method as set forth in claim 1 comprising chlorosulfonating 2,3,7,8-tetramethoxyphenoxathiine 10,10-dioxide to produce 2,3,7,8-tetramethoxyphenoxathiine-4,6-disulfonic acid 10,10-dioxide.

6. The method as set forth in claim 1 comprising chlorosulfonating 2,3,7,8-tetramethoxy-10,10-dimethyl-10H-phenoxasiline to produce 2,3,7,8-tetramethoxy-10,10-dimethyl-10H-phenoxasiline-4,6-disulfonic acid.

7. The method as set forth in claim 1 comprising chlorosulfonating 1,1'-oxybis(3,4-dimethoxybenzene) to produce 2,2'-oxybis(4,5-dimethoxybenzenesulfonyl chloride).

8. The method as set forth in claim 7 further comprising reacting said 2,2'-oxybis(4,5-dimethoxybenzenesulfonyl chloride) with triethylamine to produce diethyl 2,2'-oxybis(4,5-dimethoxybenzenesulfonate).

9. The method as set forth in claim 8 furthermore comprising reacting said diethyl 2,2'-oxybis(4,5-dimethoxybenzenesulfonate) with tetrabutylammonium iodide to produce bis-tetrabutylammonium 2,2'-oxybis(4,5-dimethoxybenzenesulfonic acid) salt.

10. The method as set forth in claim 9 furthermore comprising polymerizing said bis-tetrabutylammonium 2,2'-oxybis(4,5-dimethoxybenzenesulfonic acid) salt to produce a polymer; and acidifying said polymer to produce an acidic membrane.

11. The method as set forth in claim 10 furthermore comprising assembling a fuel cell by using said acidic membrane as a proton exchange membrane.

* * * * *